United States Patent [19]

Van der Knaap

[11] Patent Number: Plant 6,333

[45] Date of Patent: Oct. 11, 1988

[54] CHRYSANTHEMUM PLANT NAMED LUCKY STRIKE

[75] Inventor: Jacques C. M. Van der Knaap, De Lier, Netherlands

[73] Assignee: Fides Beheer B.V., De Lier, Netherlands

[21] Appl. No.: 932,794

[22] Filed: Nov. 20, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Lucky Strike particularly characterized by its flat capitulum form and single daisy capitulum type; clear white ray floret color; diameter across the face of the capitulum of 50–70 mm; and its green to yellow disc florets.

1 Drawing Sheet

The present invention comprises a new and distinct cultivar of Chrysanthemum, botanically known as *Chrysanthemum morifolium,* Ramat., and referred to by the cultivar name Lucky Strike.

Lucky Strike is a product of a planned breeding program which had the objective of creating new chrysanthemum cultivars with single capitulum type, clear white ray floret color, nine week response, and the ability to produce commercially acceptable quality in year round cut mum programs. Such traits in combination were not present in previously available commercial cultivars.

Lucky Strike was originated from a hybridization made in a controlled breeding program in De Lier, The Netherlands in 1981. The female parent was Cassa, disclosed in a pending application of applicant. The male parent of Lucky Strike was Orca, an unpatented cultivar.

Lucky Strike was discovered and selected as one flowering plant within the progeny of the stated parentage by Jacques C. M. Van der Knaap in June 1983 in a controlled environment in De Lier, The Netherlands.

The first act of asexual reproduction of Lucky Strike was accomplished when vegetative cuttings were taken from the initial selection on Aug. 7, 1983 in a controlled environment in De Lier, The Netherlands by a technician working under formulations established and supervised by Jacques C. M. Van der Knaap. Horticultural examination of selected units initiated in the Summer of 1985 has demonstrated that the combination of characteristics as herein disclosed for Lucky Strike are firmly fixed and are retained through successive generations of asexual reproduction.

Lucky Strike has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial practice.

The following traits have been repeatedly observed and are determined to be basic characteristics of Lucky Strike, which, in combination, distinguish this chrysanthemum as a new and distinct cultivar:

1. Flat capitulum form.
2. Single capitulum type.

3. Clear white ray floret.
4. Diameter across the face of the capitulum 50–70 mm.
5. Green (immature) to yellow (mature) disc florets.

Of the many commercial cultivars known to the present inventor, the most similar in comparison to Lucky Strike is Cassa, the maternal parent. When compared with Cassa, Lucky Strike has longer and narrower ray florets which are more reflexed, better growth, a longer response period, a somewhat larger overall flower diameter, and larger leaf size.

The accompanying photographic drawing shows typical inflorescence and foliage characteristics of Lucky Strike, with colors being as nearly true as possible with illustrations of this type.

In the following description, color references are made to The Royal Horticultural Society Colour Chart. The color values were determined between 11:00 a.m. and 12:00 noon in August 1986 under natural daylight at De Lier, The Netherlands.

Classification:

*Botanical.*—*Chrysanthemum morifolium,* Ramat., cv. Lucky Strike.

*Commercial.*—Cut daisy spray.

INFLORESCENCE

A. Capitulum:

*Form.*—Flat.

*Type.*—Daisy.

*Diameter across face.*—50–70 mm.

B. Corolla of ray florets:

*Color (general tonality from a distance of three meters).*—White.

*Color (upper surface.).*—155D.

*Color (under surface).*—155D.

C. Corolla of disc florets:

*Color (mature).* —Yellow.

*Color (immature).*—Green.

D. Reproductive organs:

*Androecium.*—Present only in disc florets; numerous.

*Gynoecium.*—Present in both ray and disc florets; numerous.

PLANT

A. General appearance:

*Height.*—90 cm.

B. Foliage:

*Color (upper surface).*—147A.

*Color (under surface).*—147B.

I claim:

1. A new and distinct chrysanthemum plant named

Lucky Strike, as described and illustrated, and particularly characterized by its flat capitulum form and single daisy capitulum type; clear white ray floret color; diameter across the face of the capitulum of 50–70 mm; and its green to yellow disc florets.

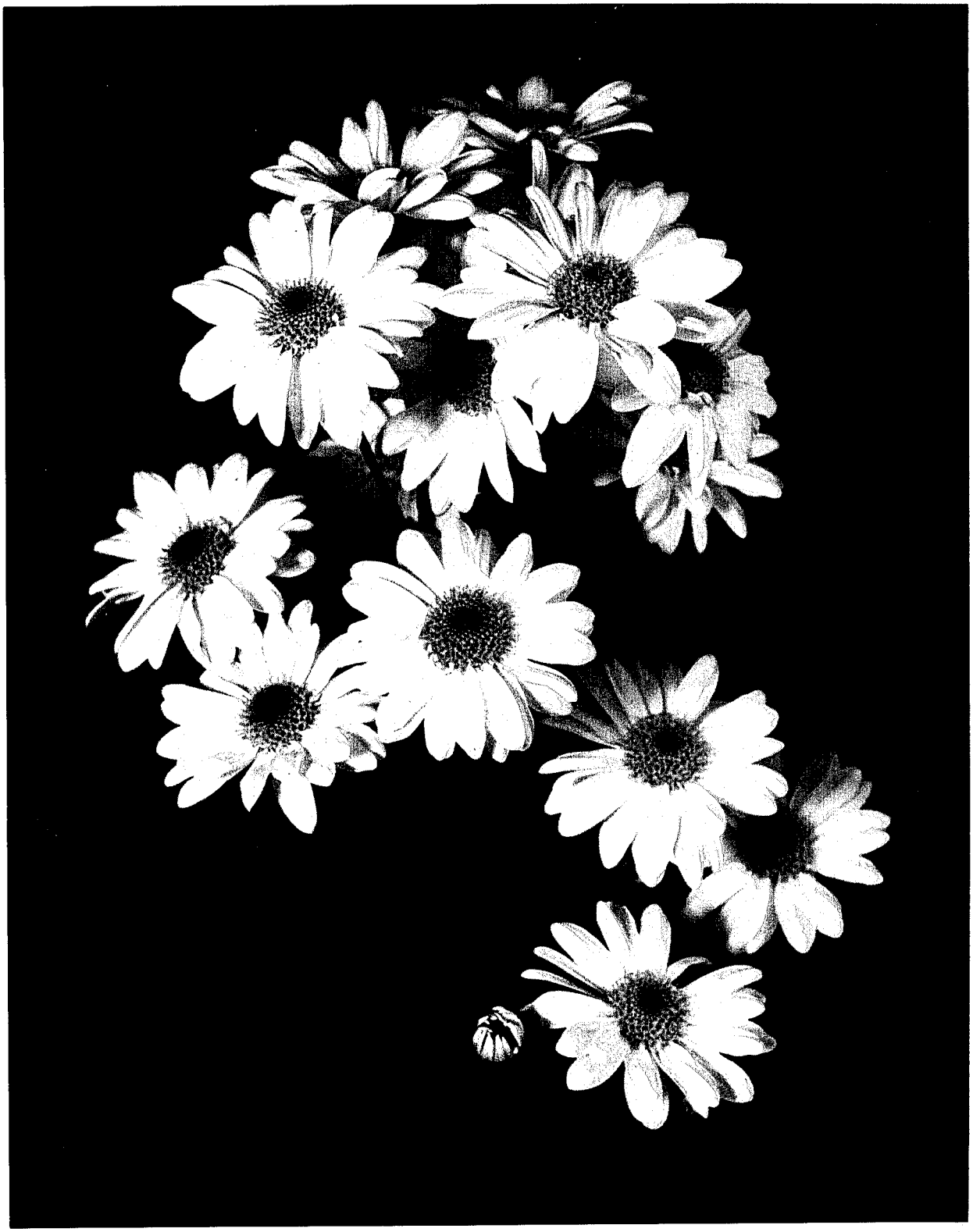

* * * * *